US008908992B1

(12) United States Patent
Rodriguez-Valderrama et al.

(10) Patent No.: US 8,908,992 B1
(45) Date of Patent: Dec. 9, 2014

(54) SYSTEM AND METHODS OF REGULARIZED OPTIMIZATION FOR MATRIX FACTORIZATION AND IMAGE AND VIDEO RECONSTRUCTION

(75) Inventors: Paul A. Rodriguez-Valderrama, Lima (PE); Marios Stephanou Pattichis, Albuquerque, NM (US); Victor Manuel Murray-Herrera, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 907 days.

(21) Appl. No.: 13/084,781

(22) Filed: Apr. 12, 2011

(51) Int. Cl.
G06K 9/36 (2006.01)
(52) U.S. Cl.
USPC .......................................... 382/276; 382/254
(58) Field of Classification Search
None
See application file for complete search history.

(56) References Cited

PUBLICATIONS

Paul Rodriguez, Victor Murray, and Mario Pattichis, "A Regularized Optimization Approach for AM-FM Reconstructions", Signals, Systems and Computers, Nov. 2010, pp. 219-221, Pacific Grove, CA.
Paul Rodriguez, "A Non-Negative Quadratic Programming Approach to Minimize the Generalized Vector-Valued Total Variation Functional," European Signal Processing Conference, Aug. 2010, pp. 314-318, ISSN 2076-1465, Aalborg, Denmark.
V. Murray, P. Rodriguez, and M. Pattichis, "Multiscale AM-FM Demodulation and Image Reconstruction Methods with Improved Accuracy," IEEE TIP, May 2010, pp. 1138-1152, vol. 19, No. 5.
Paul Rodriguez, Victor Murray, and Mario Pattichis, "A Regularized Optimization Approach for AM-FM Reconstructions", SIAM Imaging Science conference, EE.UU, Apr. 2010, Chicago, IL.
Paul Rodriguez and Brendt Wohlberg, "A Generalized Vector-Valued Total Variation Algorithm," IEEE International Conference on Image Processing (ICIP), Nov. 2009, pp. 1309-1312, Cairo, Egypt.
Paul D. O'Grady, and Scott T. Rickard, "Recovery of Non-Negative Signals from compressively Sampled Observations Via Non-Negative Quadratic Programming," Signal Processing with Adaptive Sparse Structured Representations, Mar. 2009, Ver. 1-19, Belfield, Dublin 4, Ireland.
Victor Manuel Murray Herrera, "AM-FM Methods for Image and Video Processing", Ph.D. thesis, University of New Mexico (UNM), Dec. 2008, Albuquerque, NM.
Fei Sha, Yuanqing Lin, Lawrence K. Saul, and Daniel D. Lee, "Multiplicative Updates for Nonnegative Quadratic programming," Neural Computation, 2007, pp. 2004-2031, vol. 19, No. 8.
J. L. Starck, M. Elad, and D. L. Donoho, "Image Decomposition via the Combination of Sparse Representations and a Variational Approach," IEEE TIP, Oct. 2005, pp. 1570-1582, vol. 14, No. 10.
Paul Rodriguez, "Fast and Accurate AM-FM Demodulation of Digital Images with Applications," PhD thesis, University of New Mexico (UNM), Jul. 2005, Albuquerque, NM, USA.

(Continued)

*Primary Examiner* — Chan Park
*Assistant Examiner* — Mark Roz
(74) *Attorney, Agent, or Firm* — Valauskas Corder LLC

(57) ABSTRACT

An image and video processing system and methods based on amplitude-modulation frequency-modulation ("AM-FM") demodulation to provide high quality reconstructions, both visually and quantitatively. The system and methods reconstructs an image based on a Regularized Optimization ("RO") of estimates to attain a small number of locally coherent components and simultaneously enforce a piecewise smooth constrain for one or more amplitude functions.

7 Claims, 5 Drawing Sheets

(56) References Cited

PUBLICATIONS

Z. Wang, A. Bovik, H. Sheikh, and E. Simoncelli, "Image Quality Assessment: From Error Visibility to Structural Similarity," IEEE TIP, Apr. 2004, pp. 1-14, vol. 13, No. 4.

G. Girolami and D. Vakman, "Instantaneous Frequency Estimation and Measurement: A Quasi-Local Method," Measurement Science and Technology, Jun. 2002, pp. 909-917, vol. 13.

J. P. Havlicek, D. S. Harding, and A. C. Bovik, "Multidimensional Quasi-Eigenfunction Approximations and Multicomponent AM-FM models," IEEE TIP, Feb. 2000, pp. 227-242, vol. 9, No. 2.

Daniel D. Lee, and H. Sebastian Seung, "Algorithms for Non-Negative Matrix Factorization," in Proceedings of the Conference on Neural Information Processing Systems (NIPS), 2000, pp. 556-562.

Bhaskar D. Rao, and Kenneth Kreutz-Delgado, "An Affine Scaling Methodology for Best Basis Selection," IEEE TSP, Jan. 1999, pp. 187-200, vol. 47, No. 1.

J. P. Havlicek, "AM-FM Image Models," PhD thesis, The University of Texas, Nov. 8, 1996, Austin, TX.

A. Bonnet, "On the Regularity of Edges in Image Segmentation," Annales De L' Institute Henri Poincaré, Section (C) Analyse Non linéaire,1996, pp. 485-528, vol. 13, No. 4.

5A (Original)

5B (CCA)

5C (DCA)

5D (RO)

SYSTEM AND METHODS OF REGULARIZED OPTIMIZATION FOR MATRIX FACTORIZATION AND IMAGE AND VIDEO RECONSTRUCTION

FIELD OF THE INVENTION

The present invention relates generally to image and video processing. More particularly, the present invention is directed to a system and methods of optimizing Amplitude-Modulation Frequency-Modulation ("AM-FM") demodulation for processing stationary and non-stationary image and video content.

AM-FM demodulation is useful in a variety of contexts and applications including, for example, characterization and classification of image and video from imaging modalities such as electron microscopy, spectral and hyperspectral devices, ultrasound, magnetic resonance imaging ("MRI"), positron emission tomography ("PET"), histology, color and monochrome images, molecular imaging, radiographs ("X-rays"), computer tomography ("CT"), and others. The specific applications are in fingerprint identification, detection and diagnosis of retinal disease, malignant cancer tumors, cardiac image segmentation, atherosclerosis characterization, brain function, histopathology specimen classification, characterization of anatomical structure tracking such as carotid artery walls and plaques or cardiac motion and as the basis for computer-aided diagnosis to name a few.

BACKGROUND OF THE INVENTION

Image and video processing are forms of signal processing. Signal processing allows a set of characteristics or parameters related to the image or video to be obtained. Signal processing including analog signal processing, discrete time signal processing, and digital signal processing, which may involve a one-dimensional ("1D"), two-dimensional ("2D") or three-dimensional ("3D") input signal to which signal processing techniques are applied.

Signal processing techniques include transform-based processing such as discrete or integral transforms which were implemented prior to AM-FM processing. As an example, a 1D analysis of transform-based processing includes the use of short-time Fourier Transform ("STFT") for non-stationary signals. When using STFT, the fast Fourier Transform ("FFT") of different time intervals of the signals is used to determine the frequency and phase content. Thus, the STFT is a convenient 2D representation that provides frequency content information at different time intervals. A disadvantage is that the STFT cannot be effectively generalized to images and videos. For example, using STFT for images would produce a four-dimensional ("4D") representation and using STFT for video would produce a six-dimensional ("6D") representation.

The discrete Wavelet Transform ("DWT") has also been used for transform-based image processing. Unlike Fourier Transforms, Wavelet Transforms are based on specific functions defined at different scales and durations. Thus, the DWT is a space-frequency representation of the input signal and it is related to harmonic analysis is as in Fourier Transform. While FFT uses equally spaced frequency division, DWT uses logarithmic divisions of the frequency. A disadvantage is that DWT does not measure frequency content directly.

The development of accurate methods for estimating amplitude-modulation frequency-modulation image decompositions is of great interest due to is potentially significant impact on image analysis applications including in the areas of signal, image and video processing. Applications in signal processing include speech signal analysis. Image processing applications include shape from shading, image pattern analysis, image interpolation, fingerprint classification, image retrieval in digital libraries, image segmentation, and damaged image texture repairs. Applications in video processing include cardiac image segmentation, motion estimation, and motion reconstruction, to name a few.

A number of techniques exist to reconstruct an image from its AM-FM representation in terms of amplitude, phase and frequency functions. Reconstruction of an image involves estimating or computing the amplitude, phase and frequency components of the signals emerging from each filter channel and using these components to create an AM-FM representation that best approximate the original image signal. Generally, the more components and channels used, the more information is recovered, the better the image signal is restored and the better the image is regenerated. If every component of every channel is used, this will yield to the best reconstruction of the original image. However, such approaches lead to very redundant representations that can lead to very inefficient applications in image analysis. Thus, the goal of an efficient reconstruction process is select few channels and components that best approximates the image signal.

The AM-FM Dominant Component Analysis ("DCA") and Channelized Component Analysis ("CCA") are methods used that consist of applying a filterbank to the Hilbert-transformed image, and then applying AM-FM demodulation of each bandpass filtered image. Using DCA, every pixel delivers estimated modulating functions corresponding to the AM-FM component that is locally dominant at that pixel. Using CCA, a filterbank partitions the image into components on a spatially global basis. Each resulting AM-FM component is restricted to lie in a single channel over the entire image domain. With CCA, the number of components in the computed image model is necessarily equal to the number of channels in the filterbank. AM-FM reconstructions based on the CCA use a reasonably small number of locally coherent components. In contrast, those based on the DCA only use one component—the estimates from the channel with the maximum amplitude estimate. A disadvantage of DCA and CCA are that they are known to produce noticeable visual artifacts.

Optimizing the quality of an AM-FM reconstruction image is important due to the potentially significant impact on various applications. Thus, there is demand for high quality reconstructions in both stationary and non-stationary processing for use in a variety of contexts and applications. The present invention satisfies this demand.

SUMMARY OF THE INVENTION

The present invention provides a system and methods of high quality reconstructions, both visually and quantitatively, when compared to standard reconstructions using various prior art techniques such as Dominant Component Analysis ("DCA") and Channelized Component Analysis ("CCA"). The present invention is based on a Regularized Optimization ("RO") to attain a small number of locally coherent components and simultaneously enforce a piecewise smooth constrain for one or more amplitude functions. In one embodiment, the small number of locally coherent components and piecewise smooth constrain for one or more amplitude functions is based on the estimates from the CCA. Image content from image signal components is obtained from processing a Hilbert-transformed image through a filter bank. More particularly, the present invention provides a Regularized Optimization ("RO") method of reconstructing an image by applying an amplitude-modulation frequency-modulation ("AM-FM") demodulation process to an image.

Although the present invention is discussed herein with respect to two-dimensional ("2D") images, signals, and digital videos, it is contemplated the present invention can be extended to any dimensional ("ND") images, signals and digital videos including three-dimensional ("3D").

The AM-FM representation of images permits non-stationary image content to be modeled in terms of amplitude and phase functions using the following equation:

$$b(\xi) = \sum_{n=1}^{L} a_n(\xi)\cos(\varphi_n(\xi)) \qquad (1)$$

Where $b(\xi): \mathbb{R}^2 \to \mathbb{R}$ is the input image, $\xi=(\xi_1,\xi_2)\in\mathbb{R}^2$, $L\in\mathbb{N}$, $\alpha_n:\mathbb{R}^2\to[0,\infty)^-$, and $\phi_n:\mathbb{R}^2\to\mathbb{R}$. The interpretation of Equation (1) suggest that the L AM-FM component images $\alpha_n(\xi)\cdot\cos(\phi_n(\xi))$, model the essential image modulation structure, the amplitude functions $\alpha_n(\xi)$ model stow-changing image intensity variations, and the FM components cos $(\phi_n(\xi))$ capture cast-changing image intensity variations.

It is contemplated that Equation (1) can also be interpreted as a separation of texture—FM components $\cos(\phi_n(\xi))$—from piecewise smooth content—amplitude functions $\alpha_n(\xi)$—in an image.

The AM-FM Dominant Component Analysis ("DCA") and Channelized Component Analysis ("CCA") consist of applying a collection of filterbanks—bandpass filters—to the original input image. The AM-FM demodulation of each bandpass filtered image provides estimations of instantaneous amplitude ("IA") functions $\alpha_n(\xi)$, instantaneous phase ("IP") functions $\phi_n(\xi)$, and instantaneous frequency ("IF") functions $\omega_n(\xi)=\nabla\phi_n(\xi)$.

The goal using CCA is to obtain a reasonably small number of locally coherent components such as modeling the input image as in Equation (1). The goal using DCA is to select the estimates from the channel with the maximum amplitude estimate using one component—the dominant component—to model the input image.

According to the present invention, the minimum of the following:

$$J(a,\zeta) = \frac{1}{p}\|f(a,\zeta)-b\|_p^p + \lambda_a T(a) + \lambda_\zeta \|\zeta\|_1, \text{ s.t. } a \geq 0, |\zeta| \leq 1 \qquad (2)$$

attains a small number of locally coherent components and simultaneously enforces a piecewise smooth constrain for $\alpha_n(\xi)$.

As used herein $a_n$, $\zeta_n$ and b are one-dimensional ("1D") vectors representing the two-dimensional ("2D") instantaneous amplitude function $\alpha_n(\xi)$, the two-dimensional function $\cos(\phi_n(\xi))$ and the image $b(\xi)$. In Equation (2), a equals $$[a_1^T, a_2^T, \ldots a_L^T]^T, \zeta$$

equals $$[\zeta_1^T, \zeta_2^T, \ldots, \zeta_L^T]^T,$$

and f(a,ζ) equals $$\sum_{n=1}^{L} \text{diag}(a_n) * \zeta_n.$$

The TV regularization generalization to vector-valued images with coupled channels is $$T(a) = \frac{1}{q}\left\|\sqrt{\sum_n (D_x a_n)^2 + (D_y a_n)^2}\right\|_q^q.$$

Horizontal discrete derivative operators are represented by $D_x$ and vertical discrete derivative operators are represented by $D_y$.

The present invention is useful in a variety of contexts and applications, and allows the identification of disease at different stages, such as retinal disease (diabetic retinopathy, age-related macular degeneration, glaucoma, etc.), pulmonary diseases (pneumoconiosis, lung nodules tumors, etc.), breast cancer, cellular abnormalities, or any pathological structure in a medical or biomedical image or video.

The present invention and its attributes and advantages will be further understood and appreciated with reference to the detailed description below of presently contemplated embodiments, taken in conjunction with the accompanying Figures.

DETAILED DESCRIPTION OF EMBODIMENTS OF THE INVENTION

Figure 1:
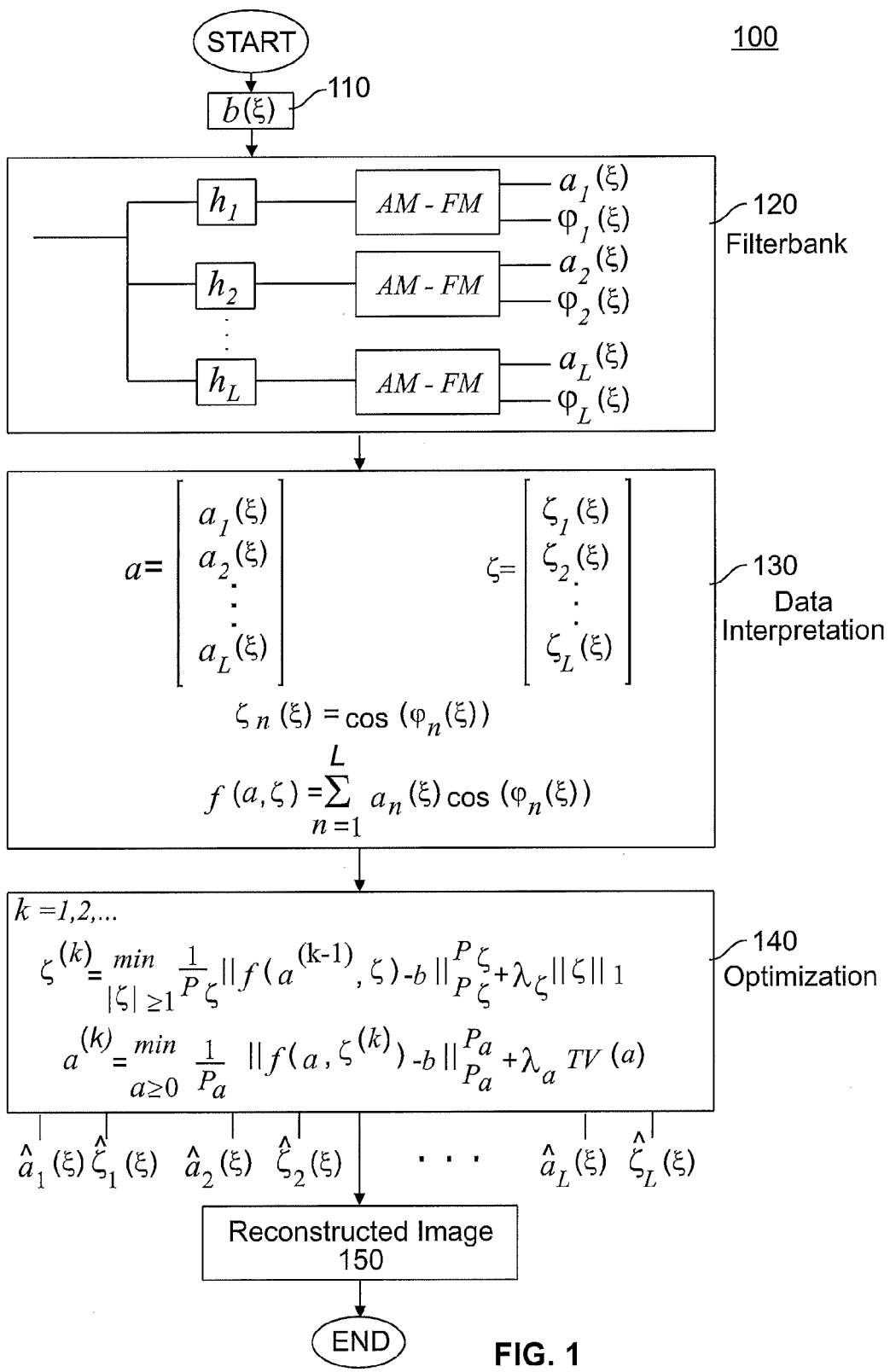
FIG. 1 illustrates a block diagram of one embodiment of AM-FM reconstruction according to the present invention.

FIG. 1 illustrates a block diagram of AM-FM reconstruction 100 according to the present invention. Specifically, FIG. 1 illustrates the solution to the minimization problem:

$$J(a,\zeta) = \frac{1}{p}\|f(a,\zeta)-b\|_p^p + \lambda_a T(a) + \lambda_\zeta \|\zeta\|_1, \text{ s.t. } a \geq 0, |\zeta| \leq 1 \qquad (2)$$

An input image signal is provided at step 110, although it is contemplated that an input video may also be provided. Enforcing two constrains in the AM-FM reconstruction, a small number of locally coherent components and a piecewise smooth constrain for the amplitude functions $b(\xi)$ in the following equation:

$$b(\xi) = \sum_{n=1}^{L} a_n(\xi)\cos(\varphi_n(\xi)) \quad (1)$$

is desired.

An extended analytic signal of the input image is computed at step 120 by applying a Hilbert transform to form a 2D extension analytic signal $b(\xi)$ of the 1D analytic signal. The extended analytic signal is processed through the filterbank and data is interpreted at step 130.

The functional $J(a,\zeta)$ is convex in a or $\zeta$; but is not necessarily convex in both variables together. In one embodiment of the invention, the numerical value of the local minimum may be solved by an optimization procedure shown in step 140 for which updates are alternated for each independent variable.

In one embodiment, the optimization procedure shown in step 140 is summarized by the following Equation (3) and Equation (4), for k=1, 2, . . . :

$$\zeta^{(k)} = \min_{|\zeta| \leq 1} \frac{1}{p_\zeta} \|f(a^{(k-1)}, \zeta) - b\|_{p_\zeta}^{p_\zeta} + \lambda_\zeta \|\zeta\|_1 \quad (3)$$

$$a^{(k)} = \min_{a \geq 0} \frac{1}{p_a} \|f(a, \zeta^{(k)}) - b\|_{p_a}^{p_a} + \lambda_a T(a) \quad (4)$$

to solve Equation (2). Specifically, $\zeta^{(k)}$ of Equation (3) can be solved based on the non-negative quadratic programming optimization algorithm and the FOCUSS algorithm. $a^{(k)}$ of Equation (4) can be solved using the vector valued IRN-NQP (vv-IRN-NQP) algorithm which is based on the non-negative quadratic programming optimization algorithm and on the iteratively reweighted norm ("IRN") algorithm for vector-valued images.

Solving for $\zeta^{(k)}$ of Equation (3) and $a^{(k)}$ of Equation (4) to ultimately solve for Equation (2) is strongly dependent on the accuracy of the initial instantaneous amplitude estimates, for example, $a^{(0)}$ is the instantaneous amplitude estimate from CCA. In one embodiment of the invention, the instantaneous amplitude estimate is obtained by the Quasi-Local Method ("QLM") and is preferred over the Quasi-Eigen Approximately ("QEA") method since the instantaneous estimates using QLM are less sensitive to perturbations—i.e., noise—than the instantaneous amplitude estimates of QEA. After optimization at step 140, the image is reconstructed at step 150.

Figure 2:
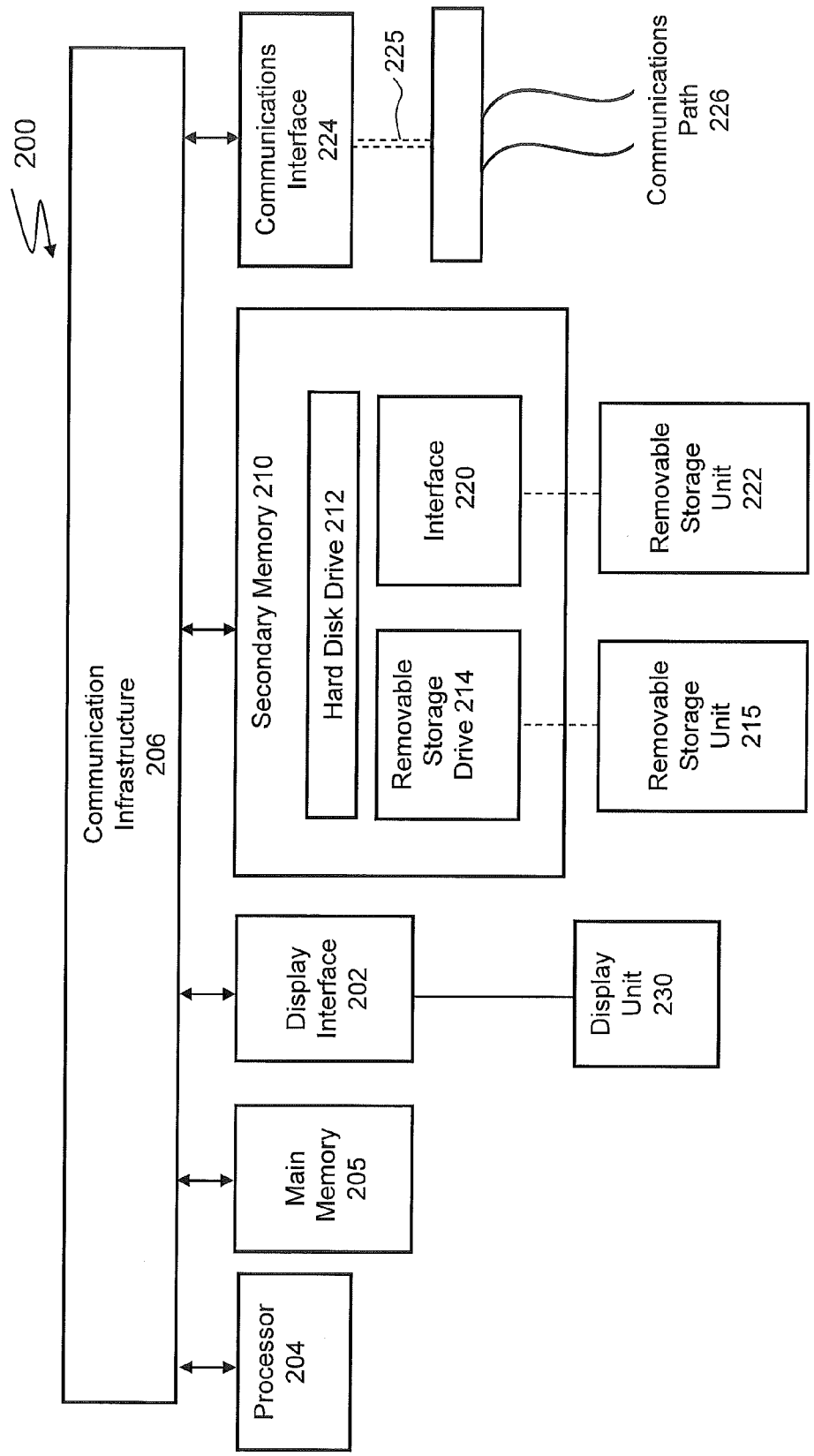
FIG. 2 illustrates a block diagram of an exemplary computer system for implementing the methods according to the present invention.

FIG. 2 illustrates an exemplary computer system 200, or network architecture, that may be used to implement the methods according to the present invention. One or more computer systems 200 may carry out the methods presented herein as computer code. One or more processors, such as processor 204, which may be a special purpose or a general-purpose digital signal processor, is connected to a communications infrastructure 206 such as a bus or network. Computer system 200 may further include a display interface 202, also connected to communications infrastructure 206, which forwards information such as graphics, text, and data, from the communication infrastructure 206 or from a frame buffer (not shown) to display unit 230. Computer system 200 also includes a main memory 205, for example random access memory ("RAM"), read-only memory ("ROM"), mass storage device, or any combination thereof. Computer system 200 may also include a secondary memory 210 such as a hard disk drive 212, a removable storage drive 214, an interface 220, or any combination thereof. Computer system 200 may also include a communications interface 224, for example, a modem, a network interface (such as an Ethernet card), a communications port, a PCMCIA slot and card, wired or wireless systems, etc.

It is contemplated that the main memory 205, secondary memory 210, communications interface 224, or a combination thereof function as a computer usable storage medium, otherwise referred to as a computer readable storage medium, to store and/or access computer software and/or instructions.

Removable storage drive 214 reads from and/or writes to a removable storage unit 215. Removable storage drive 214 and removable storage unit 215 may indicate, respectively, a floppy disk drive, magnetic tape drive, optical disk drive, and a floppy disk, magnetic tape, optical disk, to name a few.

In alternative embodiments, secondary memory 210 may include other similar means for allowing computer programs or other instructions to be loaded into the computer system 200, for example, an interface 220 and a removable storage unit 222. Removable storage units 222 and interfaces 220 allow software and instructions to be transferred from the removable storage unit 222 to the computer system 200 such as a program cartridge and cartridge interface (such as that found in video game devices), a removable memory chip (such as an EPROM, or PROM) and associated socket, etc.

Communications interface 224 allows software and instructions to be transferred between the computer system 200 and external devices. Software and instructions transferred by the communications interface 224 are typically in the form of signals 225 which may be electronic, electromagnetic, optical or other signals capable of being received by the communications interface 224. Signals 225 are provided to communications interface 224 via a communications path 226. Communications path 226 carries signals 225 and may be implemented using wire or cable, fiber optics, a phone line, a cellular phone link, a Radio Frequency ("RF") link or other communications channels.

Computer programs are stored in main memory 205 and/or secondary memory 210. Computer programs may also be received via communications interface 224. Computer programs, when executed, enable the computer system 200, particularly the processor 204, to implement the methods according to the present invention. The methods according to the present invention may be implemented using software stored in a computer program product and loaded into the computer system 200 using removable storage drive 214, hard drive 212 or communications interface 224. The software and/or computer system 200 described herein may perform any one of, or any combination of, the steps of any of the methods presented herein. It is also contemplated that the methods according to the present invention may be performed automatically, or may be invoked by some form of manual intervention.

The invention is also directed to computer products, otherwise referred to as computer program products, to provide software to the computer system 200. Computer products store software on any computer useable medium. Such software, when executed, implements the methods according to the present invention. Embodiments of the invention employ any computer useable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems ("MEMS"), nanotechnological storage device, etc.), and communication mediums (e.g., wired and wireless communications networks, local area networks, wide area networks, intranets, etc.). It is to be appreciated that the embodiments described herein can be implemented using software, hardware, firmware, or combinations thereof.

The computer system 200, or network architecture, of FIG. 2 is provided only for purposes of illustration, such that the present invention is not limited to this specific embodiment. It is appreciated that a person skilled in the relevant art knows how to program and implement the invention using any computer system or network architecture.

The performance of the present invention in terms of image reconstruction quality was compared with that of several alternative approaches, including Channelized Component Analysis ("CCA"), Dominant Component Analysis ("DCA"), Least-Squares Reconstructions ("LESHA" and "LESHAL") and Multi-Scale Least-Squares Reconstructions ("MULTILES"). For the CCA and DCA methods, the instantaneous amplitude ("IA") was computed using QLM, the instantaneous phase ("IP") was computed using the QEA, the LESHA, LESHAL and MULTILES use QEA to estimate IA and IP. As discussed more fully below, the image reconstruction quality using Regularized Optimization ("RO") was superior.

A filterbank covering the whole frequency spectrum consisting of one low-pass and one high-pass filter is used. Each separable channel filter has support over four quadrants. To maintain support over only two quadrants needed for the QEA method, Fast Fourier Transform ("FFT") pre-filtering is used to remove support in two quadrants, for example, the two left quadrants or two right quadrants. Thus, each bandpass filter has frequency support in only two quadrants of the frequency spectrum so that, in effect, each channel filter operates over a single quadrant. The filters are designed using a min-max, equiripple approach. In a preferred embodiment, passband ripple is set at 0.017 dB and the stopband attenuation is set to 66.02 dB. Because the filterbank covers the entire spectrum, it can be expected that the instantaneous frequency will fall within the spectral support of one of the channel filters. It is assumed that local image coherency will force the instantaneous frequency estimate to fall within the passband of the dominant bandpass filter.

Figure 3:
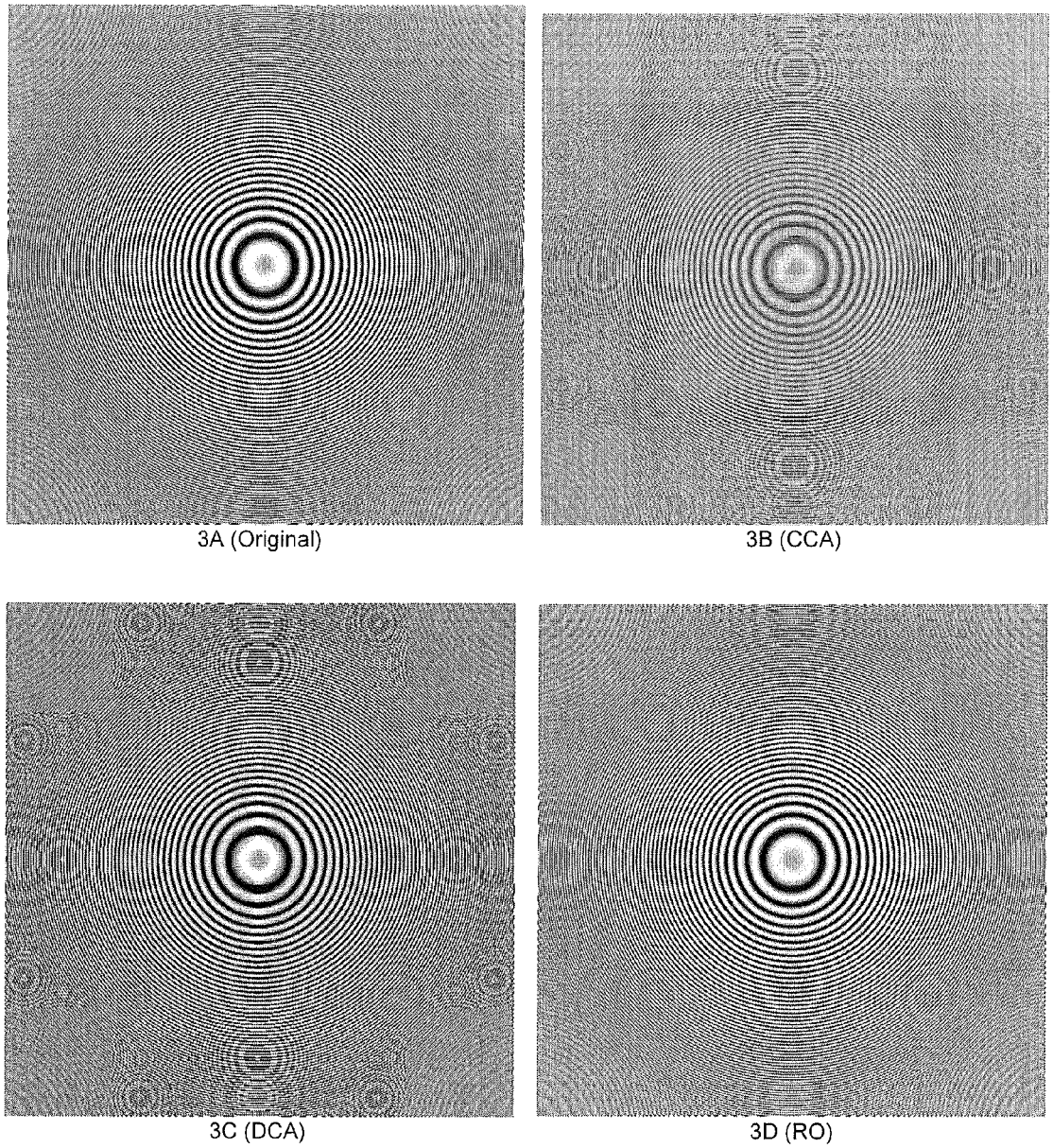
FIG. 3 illustrates an input image and reconstructions using the CCA method, the DCA method, and the method according to the present invention.
Figure 4:
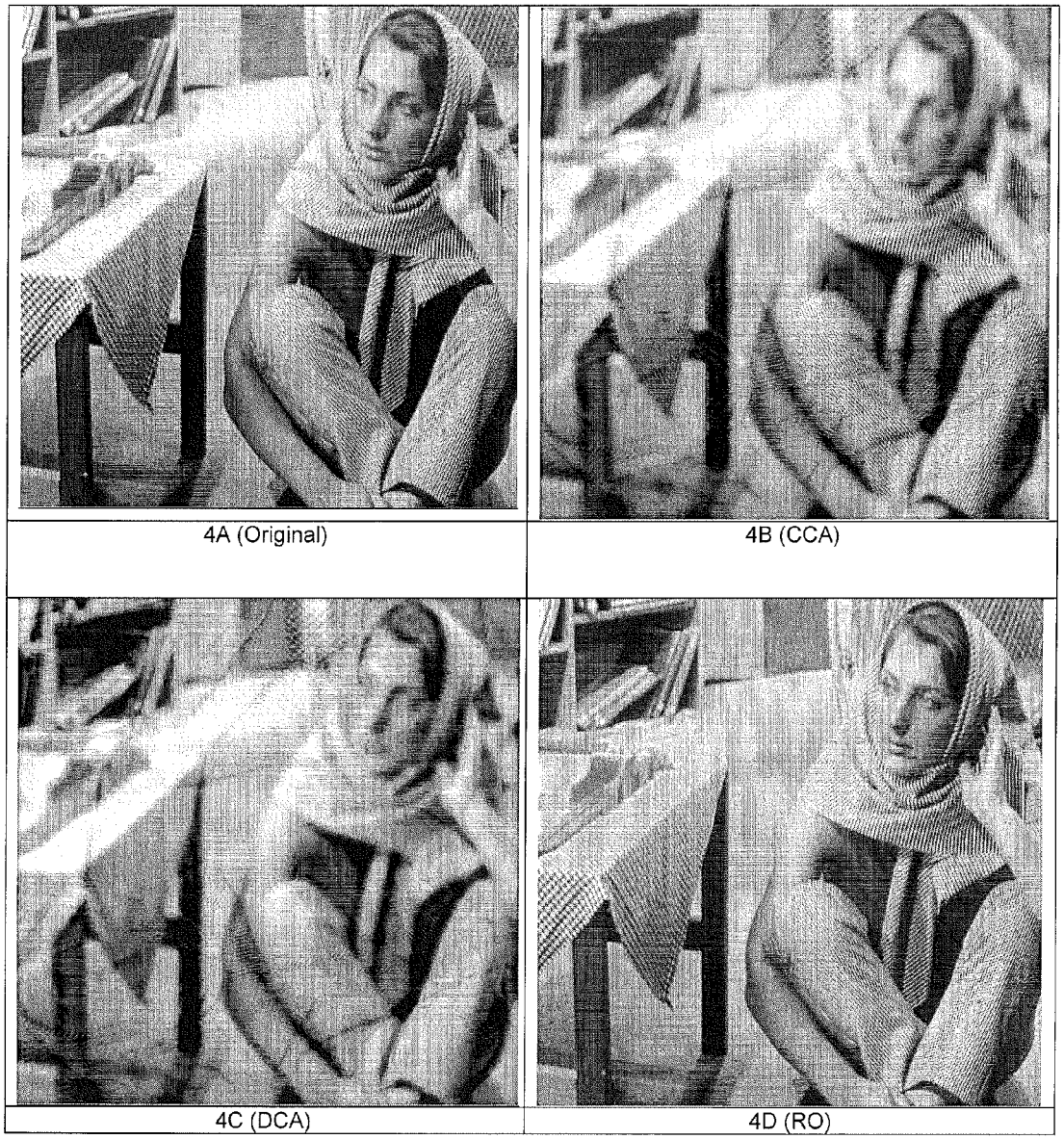
FIG. 4 illustrates an input image and reconstructions using the CCA method, the DCA method, and the method according to the present invention.
Figure 5:
FIG. 5 illustrates an input image and reconstructions using the CCA method, the DCA method, and the method according to the present invention.
Figure 5:
Figure 5:
Figure 5:

FIG. 3, FIG. 4 and FIG. 5 illustrate original input images and reconstructions using the CCA method, the DCA method, and the method according to the present invention. Specifically, FIG. 3 illustrates the "Radial Chirp" image, FIG. 4 illustrates the "Barbara" image and FIG. 4 illustrates the "Lena" image. All images contain 512×512 pixels and the simulation is carried out using Matlab-only code on a 1.83 GHz Intel Dual core CPU with a 4G RAM.

Table 1 below is a comparison of the signal to noise ratio of the reconstructed images using DCA, CCA, LESHA, LESHAL, MULTILES and the RO method (Equation (2)+ DCA) according to the present invention. Values with ( )* indicates that the reconstructed image has been normalized. For all cases, the RO approach has superior performance, especially for the gray scale photograph images Barbara and Lena (see FIG. 4 and FIG. 5). The signal-to-noise ratio is greater than 22 dB, compared with the modest signal-to-noise ratio of less than 15.2 than of all other methods for all three images tested. In no event is the signal-to-noise ratio less than 15.

TABLE 1

| | SNR (dB) | | | | | |
|---|---|---|---|---|---|---|
| Image | DCA | CCA | LESHA | LESHAL | MULTILES | (2) + DCA |
| Radial Chirp | 6.51 (14.43)* | 3.21 (−2.63)* | 0.51 | 13.56 | 13.56 | 15.41 |
| Barbara | 0.92 (7.69)* | 1.15 (9.76)* | 10.48 | 12.69 | 12.69 | 22.39 |
| Lena | 0.83 (5.38)* | 0.46 (6.58)* | 14.97 | 15.16 | 15.16 | 24.40 |

Table 2 is a comparison of the same reconstructed images using a structured similarity index ("SSIM"). SSIM measures the visual structural similarity between the reconstructed images with the original reference image. Again, the RO approach (Equation (2)+DCA) offers the highest SSIM rating, above 0.95 for all three pictures.

TABLE 2

| | SSIM index [15] | | | | | |
|---|---|---|---|---|---|---|
| Image | DCA | CCA | LESHA | LESHAL | MULTILES | (2) + DCA |
| Radial Chirp | 0.929 | 0.766 | 0.144 | 0.815 | 0.815 | 0.978 |
| Barbara | 0.730 | 0.544 | 0.619 | 0.656 | 0.656 | 0.987 |
| Lena | 0.623 | 0.378 | 0.731 | 0.731 | 0.731 | 0.962 |

The visual quality of the reconstructed images is consistent with the quantitative measurements. FIG. 3 is a side-by-side comparison of the original "Radial Chirp" image (FIG. 3A) with images reconstructed using the CCA method (FIG. 3B), the DCA method (FIG. 3C), and the RO method (FIG. 3D), respectively. Both the CCA and DCA methods create strong circular artifacts around the four edges. The contrast of the CCA reconstructed image is noticeably muted. The DCA method introduces discontinuous patches into the original continuous image. The RO method produced an image without visible artifacts, while maintaining a level of contrast and continuity comparable to the original image.

The same improved quality holds true for photographic images. FIG. 4 is a side-by-side comparison of the original "Barbara" image (FIG. 4A) with images reconstructed using the CCA method (FIG. 4B), the DCA method (FIG. 4C), and the RO method (FIG. 4D), respectively. Both the CCA and the DCA methods create visibly blurry reconstructions with artifacts of lines crossing the image at different angles. Both images lost the texture detail of the checkered tablecloth and the creases on the pants. The RO reconstruction produces a clean image with the appropriate texture without visible artifacts. A similar result is achieved in the "Lena" image shown in FIG. 5.

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A computer system method for modeling image content comprising the steps of:
   providing an input image;
   attaining a small number of locally coherent components by solving for the minimum of $$J(a, \zeta) = \frac{1}{p}\|f(a,\zeta) - b\|_p^p + \lambda_a T(a) + \lambda_\zeta \|\zeta\|_1, \ s.t. \ a \geq 0, |\zeta| \leq 1,$$

wherein
   $J(a, \zeta)$ is a function that takes vectors as inputs, and whose output is a scalar,
   a is a one dimensional column vector of image content in terms of an amplitude function,
   $\zeta$ is a one dimensional column vector of image content in terms of a cosine function applied to a phase function,
   $f(a, \zeta)$ represents a matrix-times-vector notation of the image content in terms of the amplitude function and the phase function,
   b is a one dimensional column vector of the input image approximated by the summation of a and $\zeta$,
   p is a natural and positive number representing the p-norm for finite-dimensional vector spaces,
   $\lambda_a$ represents a Lagrange multiplier of the total variation of vector a,
   T(a) refers to the total variation of vector a,
   $\lambda_\zeta$ represents a Lagrange multiplier of the vector norm of $\zeta$,
   $\|\zeta\|_1$ represents the vector norm of $\zeta$,
   s. t. represents "such that" the one dimensional column vector a is greater than or equal to zero and the absolute value of the one dimensional column vector $\zeta$ is less than or equal to one;
   enforcing a piecewise smooth constrain for one or more instantaneous amplitude functions;
   calculating a resulting amplitude function and a resulting phase function;
   reconstructing the input image using the resulting amplitude function and the resulting phase function to obtain a reconstructed image; and
   displaying the reconstructed image on a display unit.

2. The computer system method for modeling image content of claim 1 wherein said attaining step and said enforcing step are performed simultaneously.

3. The computer system method for modeling image content of claim 1 wherein said reconstructing step further comprises the step of utilizing Dominant Component Analysis.

4. The computer system method for modeling image content of claim 1 wherein said reconstructing step further comprises the step of utilizing Channelized Component Analysis.

5. The computer system method for modeling image content of claim 1 wherein said reconstructing step uses the cosine of the resulting phase function.

6. The computer system method for modeling image content of claim 1 wherein the input image is N-dimensional.

7. The computer system method for modeling image content of claim 6 wherein the input image is 2-dimensional.

* * * * *